United States Patent
Li et al.

(10) Patent No.: US 9,950,020 B2
(45) Date of Patent: Apr. 24, 2018

(54) **EXTRACTS FROM *FUSARIUM OXYSPORUM* AND USE THEREOF**

(71) Applicant: University of Macau, Macau (CN)

(72) Inventors: Shaoping Li, Macau (CN); Kun Feng, Macau (CN); Lanzhen Meng, Macau (CN); Jing Zhao, Macau (CN)

(73) Assignee: UNIVERSITY OF MACAU, Macau (CN)

( * ) Notice: Subject to any disclaimer, the term of this patent is extended or adjusted under 35 U.S.C. 154(b) by 440 days.

(21) Appl. No.: 14/384,898

(22) PCT Filed: Feb. 1, 2013

(86) PCT No.: PCT/CN2013/071258
§ 371 (c)(1),
(2) Date: Sep. 12, 2014

(87) PCT Pub. No.: WO2013/135119
PCT Pub. Date: Sep. 19, 2013

(65) Prior Publication Data
US 2015/0140029 A1      May 21, 2015

(30) Foreign Application Priority Data
Mar. 13, 2012    (CN) .......................... 2012 1 0065135

(51) Int. Cl.
*A61K 36/62*    (2006.01)
*A61K 36/062*   (2006.01)
*A61K 35/74*    (2015.01)

(52) U.S. Cl.
CPC ............ *A61K 36/062* (2013.01); *A61K 35/74* (2013.01)

(58) Field of Classification Search
None
See application file for complete search history.

(56) References Cited

U.S. PATENT DOCUMENTS

2003/0170218 A1* 9/2003 Ohhira .................. A01N 63/02
424/93.48

FOREIGN PATENT DOCUMENTS

| | | | | |
|---|---|---|---|---|
| GB | 1176999 A | * | 1/1970 | ............ C07G 11/00 |
| JP | 10313893 A | * | 12/1998 | |

* cited by examiner

*Primary Examiner* — Amy L Clark
(74) *Attorney, Agent, or Firm* — Shimokaji IP

(57) ABSTRACT

Disclosed are the action and use of water extracts and polysaccharides from *Fusarium oxysporum* in immune enhancement, which belong to the field of biological medicine. The water extracts and polysaccharides from *Fusarium oxysporum* have a significant immune enhancement effect, which can promote the proliferation of macrophages, increase the phagocytic ability of macrophages, activate macrophages to release immunological active factors NO, IL-1α and TNF-α and can be used in lower immune function diseases and tumor adjuvant treatment.

12 Claims, 1 Drawing Sheet

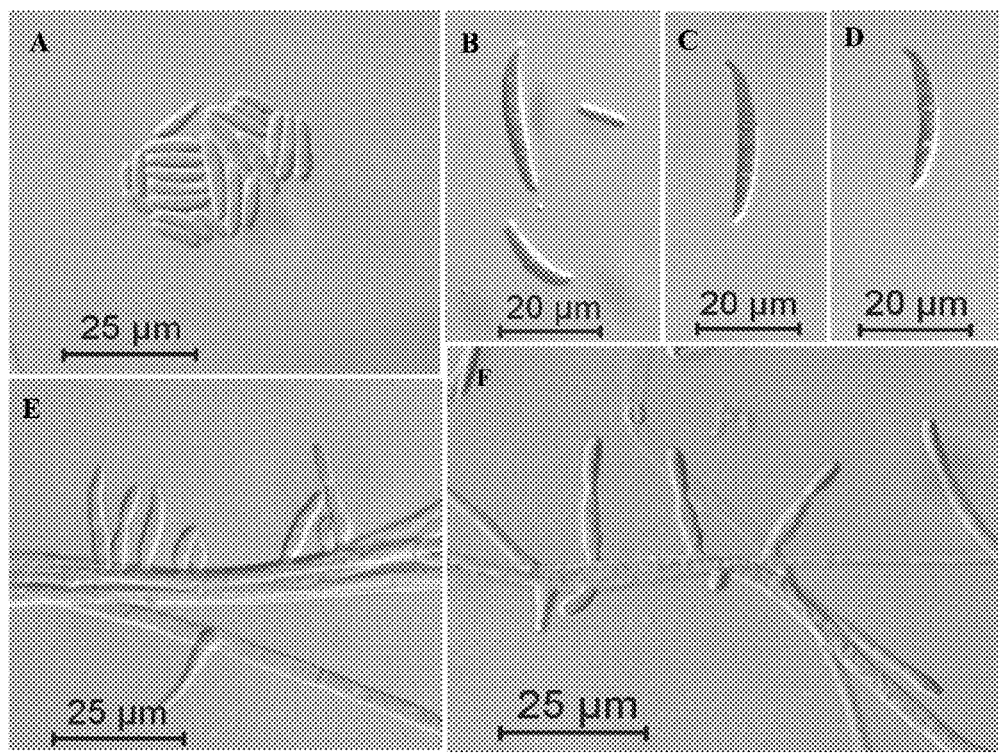

EXTRACTS FROM *FUSARIUM OXYSPORUM* AND USE THEREOF

FIELD OF THE INVENTION

The present invention relates to the field of biological medicine, and more particularly to the action and use of water extracts and polysaccharides from *Fusarium oxysporum* in immune enhancement.

BACKGROUND OF THE INVENTION

The immune system is the most important defense system for body to eliminate the invasion of pathogenic microorganisms, and eliminate senescent, injured and diseased cells, thereby, can maintain its own stability. Immune enhancement drugs can improve the biological activity of the histocyte of immune system, increase the growth of immune cells and the synthesis of antibodies in body, regulate the body's immune function, and maintain the body's environment balance, so as to improve the disease resistance of the body. At present, immune enhancement drugs has been widely used in anti-tumor, all kinds of infectious diseases and secondary immunodeficiency diseases adjuvant treatment [Hadden, J. W. Immunostimulants. *Trends in Pharmacological Sciences*, 1993, 14: 169-174]. Fungi form an important natural active compound repository, and a lot of fungi extracts and polysaccharides thereof have immune enhancement effect. Such as lentinan proves to be a kind of immunity activator, which can activate macrophages and lymphocytes. Schizophyllan has a significant cellular immune enhancement effect, and has effects on nonspecific immune system, so then can strengthen the body immunity. The schizophyllan is non-toxic, so is used for treatment of leukemia and chronic hepatitis. Therefore, the development of fungi polysaccharides for disease prevention and treatment has an important use value.

*Fusarium oxysporum* is a representative rhizosphere fungus, and is also a widespread plant endophytic fungus. Currently, the studies on the *Fusarium oxysporum* mainly concentrate in plant pathogenic mechanism, molecular biology and biological control, the latest study indicates that polysaccharides from the *Fusarium oxysporum* have in vitro antioxidant activity [Li, P., Luo, C., Sun, W., et al. In vitro antioxidant activities of polysaccharides from endophytic fungus *Fusarium oxysporum* Dzf17. *African Journal of Microbiology Research*, 2011, 5: 5990-5993], but the immune enhancement effect of the water extracts and polysaccharides from the *Fusarium oxysporum* has not been reported at home and abroad.

Macrophages are the first defense line for host to resist microbial pathogens, which are both main antigen-presenting cells and immune effector cells, can kill pathogenic microorganisms and tumor cells directly, and act an important role in the nonspecific immunity. Activated macrophages secrete nearly a hundred kinds of bioactive substances, such as NO, IL-1, TNF-α etc, these immunological active factors that act as the endogenous signals of interaction between cells play an important role in regulating the body's immune response [Adams, D. O. and Hamilton, T. A. The cell biology of macrophage activation. *Annual Review of Immunology*, 1984, 2: 283-318; Aderem, A. and Underhill, D. M. Mechanisms of phagocytosis in macrophages. *Annual Review of Immunology*, 1999, 17: 593-623]. For example, IL-1, IL-2 can promote the proliferation of T cells, promote B cells to produce antibodies, and enhance the kill ability of tumor-specific killer cells and natural killer cells. TNF-α has a direct cytotoxic effect and a growth inhibition effect to tumor cells. NO has perfectly capable of killing tumor cells and microbial pathogens. Therefore, fungi extracts or compounds that strengthen the ability of macrophages can be used in lower immune function diseases or tumor adjuvant treatment.

SUMMARY OF THE INVENTION

One objective of the present invention focuses on immune enhancement effect of water extracts and polysaccharides from fermentation mycelia of *Fusarium oxysporum*, which can be used in lower immune function diseases or tumor adjuvant treatment.

The above objective is achieved as follows:

1. The *Fusarium oxysporum* can be obtained from China General Microbiological Culture Collection Center (CGMCC) or China Agriculture Microbiological Culture Collection Center (ACCC). The morphological features of this fungus are shown in FIG. 1, 18S rRNA fragment, ITS1, 5.8S rRNA and ITS2 regions total sequences, and 28S rRNA sequence fragment of this fungus are listed below:

```
5'-gtaacaaggt ctccgttggt gaaccagcgg            60
agggatcatt accgagttta caactcccaa acccctgtga acataccttta atgttgcctc ggcggatcag   120
cccgcgcccc gtaaaacggg acggcccgcc agaggaccca aactctaatg tttcttattg    180
taacttctga gtaaaacaaa caaataaatc aaaactttca acaacggatc tcttggttct    240
ggcatcgatg aagaacgcag caaaatgcga taagtaatgt gaattgcaga attcagtgaa    300
tcatcgaatc tttgaacgca cattgcgccc gctggtattc cggcgggcat gcctgttcga    360
gcgtcatttc aaccctcaag cccccgggtt tggtgttggg gatcggctct gcccttctgg    420
gcggtgccgc ccccgaaata cattggcggt ctcgctgcag cctccattgc gtagtagcta    480
acacctcgca actggaacgc ggcgcggcca tgccgtaaaa ccccaacttc tgaatg-3'     516
```

The colony of the *Fusarium oxysporum* on PDA medium is white to pale yellow brown, and is dark red on the back. Mycelia are branched and have separations, with a width of 2~4 μm. The microspores are shaped as long oval or nearly columnar, straight or slightly curved, with size of 6.0~17 μm×2.3~3.3 μm, conidiophores are short, columnar, not branched, with size of 8.4~32.3 μm×2.5~3.9 μm. Megaspores are fusiform, most are moderate curved, and have 1-5 separations, the apical cell thereof is rostriform, and the base thereof has podocytes, with size of 23~33.4 μm×3.5~4.1 μm.

The *Fusarium oxysporum* is cultivated with liquid shake flask culture and fermentation tank culture to obtain a fungus leavening, and then the fungus leavening is centrifuged to obtain mycelia. The liquid shake flask culture and fermentation tank culture methods are the conventional fermentation culture methods in this field.

After dried and crushed, the mycelia is extracted with a hot reflux extraction method to obtain extracting solution, preferably, the temperature of the hot water is 60~140° C., and the optimized temperature is 80~100° C. The purpose of this step is to obtain the extracting solution, and all methods in this field that can improve the obtaining of the extracting solution are applicable to the present invention. In the process of extraction, the extraction is feasible in different temperature water.

After that, the extracting solution above is concentrated and dried to obtain water extracts. Concretely, the concentration and drying process can adopt the conventional concentration and drying method in this field, such as heating under normal pressure for concentration and drying method, heating under reduced pressure for concentration and drying method, and freeze drying method, etc.

Or, after concentrated, the extracting solution is precipitated with alcohol, and then centrifuged to obtain sediment, and finally the sediment is dried to obtain crude polysaccharides. Preferably, the alcohol precipitation process is processed with alcohol. Preferably, the concentration of the alcohol is 60%~100%, and the optimized is 80%~95%, preferably, the amount of the alcohol added in is 0.5~6 times, and the optimized is 2~4 times. The objective of this step is to obtain the crude polysaccharides, and other methods to obtain the crude polysaccharides from mycelia known by a person skilled in the field can replace the method of the present invention, and are included within the spirit and scope of the present invention.

2. Proliferation Ability Test (MTT Method) of Macrophages

Murine monocyte-macrophage RAW264.7 is cultivated in DMEM medium containing 10% fetal bovine serum and 1% streptomycin/penicillin, and then incubated in constant temperature incubator under the conditions of 37° C., and 5% $CO_2$. Cell suspension of the RAW264.7 macrophages is then inoculated in a 96 well culture plate with $5\times10^3$ macrophages per hole and then kept overnight, 200 μL the water extracts or crude polysaccharides of a certain concentration from *Fusarium oxysporum* are then added in, and the macrophages continue to cultivate for 24 h. The cell vitality is tested by MTT method, proliferation ability of the macrophages is calculated by the absorbance ratio of the group added with the water extracts or crude polysaccharides to blank control group.

3. Phagocytic Ability Test of Macrophages

The RAW264.7 macrophages are inoculated in a 24 well cell culture plate with $7.5\times10^5$ macrophages per hole, and 250 μL the water extracts or crude polysaccharides of different concentration from *Fusarium oxysporum* are added to each hole. Lipopolysaccharides (LPS, 400 ng/mL) and culture medium with the same volume serve as positive control group and blank control group respectively, which are incubated in incubator under the conditions of 37° C., and 5% $CO_2$ for 1 h, and then 5 μL Rainbow fluorescent particles (about $10\times10^6$ per hole) are added therein and incubated again for 2 h in dark, the culture medium is then discarded, and the remnants are washed twice with PBS, finally, cells can be collected, phagocytosis percentage (%) is tested by flow cytometry, and the result is expressed by the ratio of the phagocytosis percentage thereof to phagocytosis percentage of the blank control group.

4. Test of Immunological Active Factors Released by Macrophages

The RAW264.7 macrophages are inoculated in a 96 well cell culture plate with $6><10^4$ macrophages per hole, which are incubated in incubator under the conditions of 37° C., and 5% $CO_2$ for 24 h, after that, the water extracts or crude polysaccharides of different concentration from *Fusarium oxysporum* are added to each hole, and LPS (400 ng/mL) and culture medium with the same volume serve as positive control group and blank control group respectively. The quantity of NO released by the macrophages is tested by Griess method, the levels of TNF-α and IL-1α in cell culture supernatant are tested by ELISA kit, NO release ability (%) is calculated by the absorbance ratio of the experiment group to that of the LPS positive control group.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1 is a photograph of spores and conidiophores of *Fusarium oxysporum* according to the present invention.

Specifically, A in FIG. 1: microspores; B, C and D: megaspores; E and F: conidiophores reproducing microspores.

DETAILED DESCRIPTION OF ILLUSTRATED EMBODIMENTS

*Fusarium oxysporum* is cultivated with liquid shake flask culture and fermentation tank culture to obtain a fungus leavening, and then the fungus leavening is centrifuged to obtain mycelia. After dried and crushed, the mycelia is extracted with a hot reflux extraction method for 1 h to obtain extracting solution, and the extracting solution above is concentrated and dried to obtain water extracts. Selectively, after concentrated, the extracting solution is precipitated with alcohol, and then centrifuged to obtain sediment, and finally the sediment is dried to obtain crude polysaccharides, and the amount and the concentration of the alcohol are 4 times and 95% respectively. The effects of the water extracts and crude polysaccharides from *Fusarium oxysporum* to the function (proliferation ability, phagocytic ability, and immunologic molecules releasing) of the macrophages are studied respectively.

Embodiment 1

Murine monocyte-macrophage RAW264.7 is cultivated in DMEM medium containing 10% fetal bovine serum and 1% streptomycin/penicillin, and then incubated in constant temperature incubator under the conditions of 37° C., and 5% $CO_2$. Cell suspension of the RAW264.7 macrophages is then inoculated in a 96 well culture plate with $5\times10^3$ macrophages per hole and then kept overnight, 200 μL the water extracts or crude polysaccharides of a certain concentration from *Fusarium oxysporum* are then added in, and the macrophages continue to cultivate for 24 h. The cell vitality is tested by MTT method, proliferation ability of the macrophages is calculated by the absorbance ratio of the group added with the water extracts or crude polysaccharides to blank control group.

The results show that the water extracts or crude polysaccharides from *Fusarium oxysporum* in the concentration range of 0.5~128 μg/mL have significant effects on promoting the proliferation of the macrophages, as shown in table 1.

TABLE 1 the effects of the water extracts or crude polysaccharides
from *Fusarium oxysporum* to the proliferation
ability of macrophages RAW264.7

| sample | concentration (μg/ml) | Proliferation ratio (%) | sample | concentration (μg/ml) | Proliferation ratio (%) |
|---|---|---|---|---|---|
| water extracts | 0.5 | 97.1 ± 6.5 | polysaccharides | 0.5 | 118.3 ± 17.4 |
| | 2 | 105.4 ± 8.4 | | 2 | 137.4 ± 17.6* |
| | 8 | 122.7 ± 1.7** | | 8 | 145.4 ± 15.7** |
| | 32 | 127.9 ± 5.0* | | 32 | 138.1 ± 10.7** |
| | 128 | 118.8 ± 6.2* | | 128 | 122.9 ± 12.5* |

Data are expressed as Mean ± SEM, n = 3.
Compared to the blank control group,
*$p < 0.05$,
**$p < 0.01$○

Embodiment 2

The RAW264.7 macrophages is are inoculated in a 24 well cell culture plate with $7.5 \times 10^5$ macrophages per hole, and 250 μL the water extracts or crude polysaccharides of different concentration from *Fusarium oxysporum* are added to each hole. Lipopolysaccharides (LPS, 400 ng/mL) and culture medium with the same volume serve as positive control group and blank control group respectively, which are incubated in incubator under the conditions of 37° C., and 5% $CO_2$ for 1 h, and then 5 μL Rainbow fluorescent particles (about $10 \times 10^6$ per hole) are added therein and incubated again for 2 h in dark, the culture medium is then discarded, and the remnants are washed twice with PBS, finally, cells can be collected, phagocytosis percentage (%) is tested by flow cytometry, and the result is expressed by the ratio of the phagocytosis percentage thereof to phagocytosis percentage of the blank control group.

The results show that the water extracts or crude polysaccharides from *Fusarium oxysporum* in a certain concentration can promote the phagocytic ability of the macrophages significantly. The water extracts (300 μg/mL) promoting the phagocytic ability of the macrophages is 29.04% higher than that of the blank control group, the crude polysaccharides (500 μg/mL) promoting the phagocytic ability of the macrophages is 63.5% higher than that of the blank control group, which is equivalent to the positive control group LPS (400 ng/mL) that is 63.5% higher than the blank control group.

Embodiment 3

The RAW264.7 macrophages is are inoculated in a 96 well cell culture plate with $6 \times 10^4$ macrophages per hole, which are incubated in incubator under the conditions of 37° C., and 5% $CO_2$ for 24 h, after that, the water extracts or crude polysaccharides of different concentration from *Fusarium oxysporum* are added to each hole, and LPS (400 ng/mL) and culture medium with the same volume serve as positive control group and blank control group respectively. The quantity of NO released by the macrophages is tested by Griess method, the levels of TNF-α and IL-1α in cell culture supernatant are tested by ELISA kit, NO release ability (%) is calculated by the absorbance ratio of the experiment group to that of the LPS positive control group.

The results show that the water extracts (8~128 μg/mL) and crude polysaccharides (0.5~128 μg/mL) from *Fusarium oxysporum* can promote the macrophages to release NO significantly ($p < 0.05$) or extremely significantly ($p < 0.01$) (as shown in table 2). The water extracts and crude polysaccharides also can promote the macrophages to release immunological active factors IL-1α and TNF-α significantly (as shown in table 3).

TABLE 2 the effects of the water extracts or crude polysaccharides from
*Fusarium oxysporum* on the macrophages RAW264.7 to release NO

| sample | concentration (μg/ml) | Release quantity of NO (% LPS) | sample | concentration (μg/ml) | Release quantity of NO (% LPS) |
|---|---|---|---|---|---|
| water extracts | 0.5 | 0.4 ± 0.2 | polysaccharides | 0.5 | 49.7 ± 6.3** |
| | 2 | 4.6 ± 4.9 | | 2 | 79.4 ± 6.9** |
| | 8 | 55.2 ± 10.3* | | 8 | 89.0 ± 4.0** |
| | 32 | 92.4 ± 1.1** | | 32 | 95.6 ± 3.6** |
| | 128 | 102.8 ± 7.4** | | 128 | 105.4 ± 1.9** |

Data are expressed as Mean ± SEM, n = 3.
Compared to the blank control group,
*$p < 0.05$,
**$p < 0.01$○

TABLE 3 the effects of the water extracts or crude polysaccharides
from *Fusarium oxysporum* on the macrophages RAW264.7
to release immunological active factors

| sample | concentration (μg/ml) | immunological active factors (pg/mL) | |
|---|---|---|---|
| | | IL-1α | TNF-α |
| culture medium | 0 | 144 ± 24.2 | 5895.3 ± 163.3 |
| LPS | 0.4 | 324.5 ± 38.2* | 28970.2 ± 910.6** |
| water extracts | 0.3 | 110.5 ± 15.7 | 3014.8 ± 475.8 |
| | 3 | 236.2 ± 47* | 16168.7 ± 679.2** |
| | 30 | 327.9 ± 35.2* | 22190.8 ± 622.9** |
| polysaccharides | 0.1 | 64.2 ± 24.6 | 4699.6 ± 422.3 |
| | 0.6 | 118.1 ± 18.7 | 6207.8 ± 1515.5 |
| | 3 | 207.3 ± 56.7* | 12215.1 ± 4207.8* |
| | 15 | 236.8 ± 24.1* | 21843.6 ± 5679.5* |

Data are expressed as Mean ± SEM, n = 3.
Compared to the blank control group,
*$p < 0.05$,
**$p < 0.01$○

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A method for preparing an immune enhancement drug comprising the steps of:
    (a) cultivating *Fusarium oxysporum* with a liquid shake flask culture and fermentation tank culture to obtain a fungus leavening;
    (b) centrifuging the fungus leavening to obtain mycelia; and
    (c) extracting the mycelia to obtain the water extracts and/or the crude polysaccharides.

2. A method for preparing a drug for treating lower immune function diseases comprising the steps of:
    (a) cultivating *Fusarium oxysporum* with a liquid shake flask culture and fermentation tank culture to obtain a fungus leavening;
    (b) centrifuging the fungus leavening to obtain mycelia; and
    (c) extracting the mycelia to obtain water extracts and/or crude polysaccharides.

3. A method for preparing a drug for tumor adjuvant treatment comprising the steps of:
    (a) cultivating *Fusarium oxysporum* with a liquid shake flask culture and fermentation tank culture to obtain a fungus leavening;
    (b) centrifuging the fungus leavening to obtain mycelia; and
    (c) extracting the mycelia to obtain water extracts and/or crude polysaccharides.

4. A method for preparing an immune enhancement drug comprising *Fusarium oxysporum*, and the steps of:
    (a) cultivating *Fusarium oxysporum* with a liquid shake flask culture and fermentation tank culture to obtain a fungus leavening;
    (b) centrifuging the fungus leavening to obtain mycelia; and
    (c) extracting the mycelia to obtain water extracts and/or crude polysaccharides.

5. A method for preparing a drug for treating lower immune function diseases comprising *Fusarium oxysporum*, and the steps of:
    (a) cultivating *Fusarium oxysporum* with a liquid shake flask culture and fermentation tank culture to obtain a fungus leavening;
    (b) centrifuging the fungus leavening to obtain mycelia; and
    (c) extracting the mycelia to obtain water extracts and/or crude polysaccharides.

6. A method for preparing a drug for tumor adjuvant treatment comprising *Fusarium oxysporum*, a water extract and/or crude polysaccharides from *Fusarium oxysporum*, the method comprising the steps of:
    (a) cultivating *Fusarium oxysporum* with a liquid shake flask culture and fermentation tank culture to obtain a fungus leavening;
    (b) centrifuging the fungus leavening to obtain mycelia; and
    (c) extracting the mycelia to obtain the water extract and/or the crude polysaccharides.

7. The method according to claim 1, wherein the step (c) of extracting the mycelia to obtain the water extract and/or the crude polysaccharides further comprises:
    (d) drying and crushing the mycelia to provide a product;
    (e) extracting the product of step (d) with a hot reflux extraction to obtain an extracting solution;
    (f) concentrating and drying the extracting solution to obtain the water extract;
    (g) optionally, concentrating and precipitating the extracting solution with an to provide an alcohol product;
    (h) centrifuging the alcohol product of step (g) to obtain a sediment; and
    (i) drying the sediment to obtain the crude polysaccharides.

8. The method according to claim 2, wherein the step (c) of extracting the mycelia to obtain the water extract and/or the crude polysaccharides further comprises:
    (d) drying and crushing the mycelia to provide a product;
    (e) extracting the product of step (d) with a hot reflux extraction to obtain an extracting solution;
    (f) concentrating and drying the extracting solution to obtain the water extract;
    (g) optionally, concentrating and precipitating the extracting solution with an to provide an alcohol product;
    (h) centrifuging the alcohol product of step (g) to obtain a sediment; and
    (i) drying the sediment to obtain the crude polysaccharides.

9. The method according to claim 3, wherein the step (c) of extracting the mycelia to obtain the water extract and/or the crude polysaccharides further comprises:

(d) drying and crushing the mycelia to provide a product;
(e) extracting the product of step (d) with a hot reflux extraction to obtain an extracting solution;
(f) concentrating and drying the extracting solution to obtain the water extract;
(g) optionally, concentrating and precipitating the extracting solution with an to provide an alcohol product;
(h) centrifuging the alcohol product of step (g) to obtain a sediment; and
(i) drying the sediment to obtain the crude polysaccharides.

10. The method according to claim 4, wherein the step (c) of extracting the mycelia to obtain the water extracts and/or the crude polysaccharides further comprises:
(d) drying and crushing the mycelia to provide a product;
(e) extracting the product of step (d) with a hot reflux extraction to obtain an extracting solution;
(f) concentrating and drying the extracting solution to obtain the water extract;
(g) optionally, concentrating and precipitating the extracting solution with an to provide an alcohol product;
(h) centrifuging the alcohol product of step (g) to obtain a sediment; and
(i) drying the sediment to obtain the crude polysaccharides.

11. The method according to claim 5, wherein the step (c) of extracting the mycelia to obtain the water extract and/or the crude polysaccharides further comprises:
(d) drying and crushing the mycelia to provide a product;
(e) extracting the product of step (d) with a hot reflux extraction to obtain an extracting solution;
(f) concentrating and drying the extracting solution to obtain the water extract;
(g) optionally, concentrating and precipitating the extracting solution with an to provide an alcohol product;
(h) centrifuging the alcohol product of step (g) to obtain a sediment; and
(i) drying the sediment to obtain the crude polysaccharides.

12. The method according to claim 6, wherein the step (c) of extracting the mycelia to obtain the water extract and/or the crude polysaccharides further comprises:
(d) drying and crushing the mycelia to provide a product;
(e) extracting the product of step (d) with a hot reflux extraction to obtain an extracting solution;
(f) concentrating and drying the extracting solution to obtain the water extract;
(g) optionally, concentrating and precipitating the extracting solution with an to provide an alcohol product;
(h) centrifuging the alcohol product of step (g) to obtain a sediment; and
(i) drying the sediment to obtain the crude polysaccharides.

\* \* \* \* \*

SEQUENCE LISTING

<160> NUMBER OF SEQ ID NOS: 1

<210> SEQ ID NO 1
<211> LENGTH: 515

```
<212> TYPE: DNA
<213> ORGANISM: Fusarium oxysporum

<400> SEQUENCE: 1
gtaacaaggt ctccgttggt gaaccagcgg agggatcatt accgagttta caactcccaa        60
acccctgtga acatacctta atgttgcctc ggcggatcag cccgcgcccc gtaaaacggg       120
acggcccgcc agaggaccca aactctaatg tttcttattg taacttctga gtaaaacaaa       180
aaataaatca aaactttcaa caacggatct cttggttctg gcatcgatga agaacgcagc       240
aaaatgcgat aagtaatgtg aattgcagaa ttcagtgaat catcgaatct ttgaacgcac       300
attgcgcccg ctggtattcc ggcgggcatg cctgttcgag cgtcatttca accctcaagc       360
ccccgggttt ggtgttgggg atcggctctg cccttctggg cggtgccgcc cccgaaatac       420
attggcggtc tcgctgcagc ctccattgcg tagtagctaa cacctcgcaa ctggaacgcg       480
gcgcggccat gccgtaaaac cccaacttct gaatg                                 515
```